(12) United States Patent
Chen et al.

(10) Patent No.: US 6,281,611 B1
(45) Date of Patent: Aug. 28, 2001

(54) USE OF MOVING ELEMENT TO PRODUCE HEAT

(75) Inventors: James C. Chen, Bellevue; Darrin Huston, Enumclaw, both of WA (US)

(73) Assignee: Light Sciences Corporation, Issaquah, WA (US)

( * ) Notice: Subject to any disclaimer, the term of this patent is extended or adjusted under 35 U.S.C. 154(b) by 0 days.

(21) Appl. No.: 09/548,385

(22) Filed: Apr. 11, 2000

Related U.S. Application Data (63) Continuation-in-part of application No. 09/547,700, filed on Apr. 11, 2000, which is a continuation-in-part of application No. 09/325,022, filed on Jun. 3, 1999, now Pat. No. 6,092,531, which is a division of application No. 09/021,693, filed on Feb. 10, 1998.

(51) Int. Cl.[7] ..................................................... H05B 6/10
(52) U.S. Cl. ................... 310/171; 310/152; 310/156.01; 310/40 R; 219/201
(58) Field of Search ................................ 219/201, 209, 219/635, 634; 310/171, 40 R, 50, 46, 156, 104, 112, 103, 152

(56) References Cited

U.S. PATENT DOCUMENTS

| | | | |
|---|---|---|---|
| 2,481,196 | 9/1949 | Bulliet | 310/171 |
| 3,668,448 | 6/1972 | Hayasaka | 310/166 |

(List continued on next page.)

OTHER PUBLICATIONS

Hilton, Edgar F., et al. "Magnetic Suspension Controls for a New Continuous Flow Ventricular Assist Device." ASAIO Journal, 1977, 43:M598–M603.

Kono, Satoshi, et al. "In Vivo and In Vitro Evaluation of the Pulsatile Mode of a Magnetically Suspended Centrifugal Pump." ASAIO Journal, 1977, 43:M580–M584.

Xu, Longya, et al. "Analysis of a New PM Motor Design for a Rotary Dynamic Blood Pump." ASAIO Journal, 1997, 43:M559–M564.

Yamane, Takashi, et al. "Fluid Dynamic Characteristics of Monopivot Magnetic Suspension Blood Pumps." ASAIO Journal, 1997, 43:M635–M638.

Matsushita Electronic Components Web site. Mobile communications equipment. Online. Aug. 17, 1999. Available http://www.maco.panasonic.co.jp/htm–bin/maco/corpo/a5a_3.html. 1 pg.

(List continued on next page.)

Primary Examiner—Burton S. Mullins
(74) Attorney, Agent, or Firm—Ronald M. Anderson (57) ABSTRACT

A method and apparatus for heating substances such as beverages, soups, chemicals, etc., with heat produced by circulating electrical eddy currents. In one form of the device, a magnetic flux generating base produces a varying magnetic field by using an electric motor to move a plurality of permanent magnets. The varying magnetic field induces the eddy currents to circulate in a ferromagnetic conductor that is sealed in the bottom of a container resting on the magnetic flux generating base. Losses due to the eddy current produce heat that is transferred into the substance within the container. In another embodiment, the motor moves one or more magnetic flux shunts to vary the magnetic field experienced by the ferromagnetic conductor. The presence of the container on the magnetic flux generating base can be detected and used to control the operation of the electrical motor. An indicator is provided in one embodiment to alert a user when the electrical motor is energized and the substance in the container is being heated.

44 Claims, 6 Drawing Sheets

U.S. PATENT DOCUMENTS

| | | | | |
|---|---|---|---|---|
| 3,672,352 | | 6/1972 | Summers ............................ 128/2 R |
| 3,836,289 | | 9/1974 | Wolford et al. ...................... 417/415 |
| 3,942,535 | | 3/1976 | Schulman ...................... 128/419 PS |
| 3,967,146 | | 6/1976 | Howard ................................ 310/80 |
| 4,005,346 | | 1/1977 | Hisa .................................... 318/128 |
| 4,038,572 | | 7/1977 | Hanagan ............................... 310/46 |
| 4,038,625 | | 7/1977 | Tompkins et al. .................... 336/83 |
| 4,082,936 | * | 4/1978 | Aoki et al. ........................... 219/635 |
| 4,163,164 | | 7/1979 | Pieters ............................... 310/103 |
| 4,338,951 | | 7/1982 | Saliga ................................. 128/695 |
| 4,392,071 | | 7/1983 | Gauthier ............................ 310/113 |
| 4,432,363 | | 2/1984 | Kakegawa ..................... 128/419 PS |
| 4,443,776 | | 4/1984 | Cunningham ...................... 335/302 |
| 4,461,302 | | 7/1984 | Phillipps et al. .................... 128/630 |
| 4,507,048 | | 3/1985 | Belenger et al. ..................... 415/90 |
| 4,511,777 | * | 4/1985 | Gerard ............................... 219/634 |
| 4,564,778 | | 1/1986 | Yoshida .............................. 310/177 |
| 4,665,896 | | 5/1987 | LaForge et al. ..................... 128/1 D |
| 4,679,560 | | 7/1987 | Galbraith ........................ 128/419 R |
| 4,736,752 | | 4/1988 | Munck et al. ....................... 128/798 |
| 4,741,339 | | 5/1988 | Harrison et al. ............... 128/419 PS |
| 4,761,527 | * | 8/1988 | Mohr .................................. 219/635 |
| 4,798,926 | * | 1/1989 | Sakai .................................. 219/634 |
| 4,831,299 | | 5/1989 | Hayasaka ............................ 310/166 |
| 4,927,337 | | 5/1990 | Lustwerk ............................ 417/420 |
| 5,109,843 | | 5/1992 | Melvin et al. ................... 128/419 R |
| 5,112,200 | | 5/1992 | Isaacson et al. .................... 417/356 |
| 5,146,123 | | 9/1992 | Yarr ...................................... 310/15 |
| 5,274,207 | * | 12/1993 | Griffith ............................... 219/634 |
| 5,314,457 | | 5/1994 | Jeutter et al. ....................... 607/116 |
| 5,350,413 | | 9/1994 | Miller .................................. 607/61 |
| 5,550,452 | | 8/1996 | Shirai et al. ........................... 320/2 |
| 5,569,156 | | 10/1996 | Mussivand ............................ 600/16 |
| 5,690,851 | * | 11/1997 | Yoshioka et al. ................... 219/635 |
| 5,710,502 | | 1/1998 | Poumey .................................. 320/2 |
| 5,945,762 | | 8/1999 | Chen et al. ......................... 310/171 |
| 5,959,433 | | 9/1999 | Rohde ................................. 320/108 |
| 6,011,245 | * | 1/2000 | Bell ..................................... 219/631 |

OTHER PUBLICATIONS

Panasonic® Industrial Company Web site. OEM Communications Components (Power Supplies). Online. Aug. 17, 1999. Available http://www.panasonic.com/industrial_oem/communicat . . . /communications power supplies.ht. 1 pg.

Panasonic Design and Specifications printout. Contactless Charger. Undated. 1 pg.

TDK USA Corporation Web site. Application Notes. Online. Aug. 17, 1999. Available http://power.tdk.com/dcdc/applicat1.htm. 1 pg.

TDK. DC–DC Converter Unit brochure. Contactless Charger P/N IBC–131. Undated. 6 pp.

* cited by examiner

USE OF MOVING ELEMENT TO PRODUCE HEAT

RELATED APPLICATIONS

This application is a continuation-in-part of application Ser. No. 09/547,700 entitled "Contactless Energy Transfer Apparatus," filed Apr. 11, 2000, which is a continuation-in-part of application Ser. No. 09/325,022, filed Jun. 3, 1999, which is now U.S. Pat. No. 6,092,531 which is a divisional application of Ser. No. 09/021,693, filed on Feb. 10, 1998, U.S. Pat. No. 5,945,762 the benefit of the filing dates of which is hereby claimed under 35 U.S.C. §120.

FIELD OF THE INVENTION

The present invention generally pertains to electrically energized heating devices, and more specifically, to a heating device that heats a substance via a contactless transfer of electromagnetic energy provided by a moving magnet.

BACKGROUND OF THE INVENTION

Portable hot plates are often used for warming and maintaining the temperature of heated beverages, such as coffee, tea, hot apple cider, etc., and food such as soups. These devices are also used in the laboratory for heating substances. Hot plates generally include a supporting surface upon which the base of a container (e.g., a coffee cup, chemistry flask, etc.) is placed while undergoing heat transfer from a heat source within the hot plate. An electric resistance heating element is typically used for the heat source and dissipates enough energy to achieve a moderately high to high temperature (e.g., up to several hundred degrees C.).

A major drawback of most portable hot plates is that they represent a significant risk of burning anyone who contacts the surface that supports a container to be heated when the surface is hot. Children are especially at risk. In order to maintain a beverage such as coffee at a desired temperature, it is necessary that the heat transferred from the hot plate to the container match the heat lost from the container (and the liquid contained therein) to the environment.

Since it is desirable to keep heated beverages hot, coffee cups and the like are typically made of materials that have a relatively low thermal conductivity, such as refractory materials, glass, plastic, etc. However, the insulating properties of these materials act as an impediment in heating a beverage in the container with a hot plate. As a result, the hot plate must be maintained at a temperature much higher than the desired temperature of the beverage. This temperature is often high enough to cause moderate to severe burns to anyone who accidentally touches the hot plate when it is at its normal operating temperature.

The manner in which hot plates are typically used exacerbates the foregoing problem. Most portable hot plates have a power switch, and may also include a temperature control. In order to heat something with a hot plate, it is necessary to at least turn the power switch on and it may be necessary to set the temperature control knob to a desired setting. It is not uncommon to accidentally leave a hot plate energized after it has been used. Furthermore, even if properly turned off after use, the power switch can easily be turned on by a curious child, posing a significant safety hazard for children, as well as a potential fire hazard.

It is therefore desirable to provide a portable apparatus for heating a substance, such as a beverage or food, that does not require the use of a high temperature heat source in the apparatus. Furthermore, it is desirable that such an apparatus only operate when the substance is being heated and automatically shut off when a container containing the substance is removed from the apparatus.

SUMMARY OF THE INVENTION

In accord with the present invention, a method and apparatus are defined to enable a substance to be safely heated without using a surface that is maintained at a high temperature to transfer heat into a container for the substance. The apparatus includes a container in which the substance is disposed and the container is adapted to be supported on a surface defined by a housing for a magnetic field generator that produces a varying magnetic field. A ferromagnetic conductor, preferably comprising a "lossy" ferromagnetic material such as "soft" iron, is disposed in a base of the container. When being heated by the apparatus, the base of the container is supported by the surface. The magnetic field generator disposed in the housing includes at least one permanent magnet. A prime mover, preferably an electric motor, is drivingly coupled to an element of the magnetic field generator, causing the element of the magnetic field generator to move relative to the ferromagnetic conductor in the base of the container. Movement of the element produces a varying magnetic field that induces an electrical eddy current to circulate within the ferromagnetic conductor. This electrical eddy current generates heat due to resistive losses, increasing the temperature of the ferromagnetic conductor. Heat is transferred from the ferromagnetic conductor to the substance disposed in the container through the base, thereby heating the substance.

In one embodiment, the element of the magnetic field generator includes a plurality of permanent magnets that are mounted on a movable support. This movable support rotated or reciprocated back and forth relative to the ferromagnetic conductor, so that a magnetic field is varied along a path that includes the ferromagnetic conductor.

In another embodiment, the element of the magnetic filed generator that is drivingly coupled to the prime mover comprises a magnetic flux shunt that is moved by the prime mover and periodically shunts the magnetic field produced by the one or more permanent magnet. Movement of the magnetic flux shunt thus varies the magnetic field along a path that includes the ferromagnetic conductor.

The container preferably includes an insulation layer around its sides or the sides comprise a material with good insulating properties. The insulating layer preferably includes an external wall and internal wall made of a low thermal conductivity material and separated by an air gap.

A further aspect of the present invention is directed to a method for heating a substance by inductively coupling a varying magnetic field to a ferromagnetic conductor disposed in a container in which the substance is disposed. The steps of this method are generally consistent with the functions provided by the elements of the apparatus discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

Figure 1:
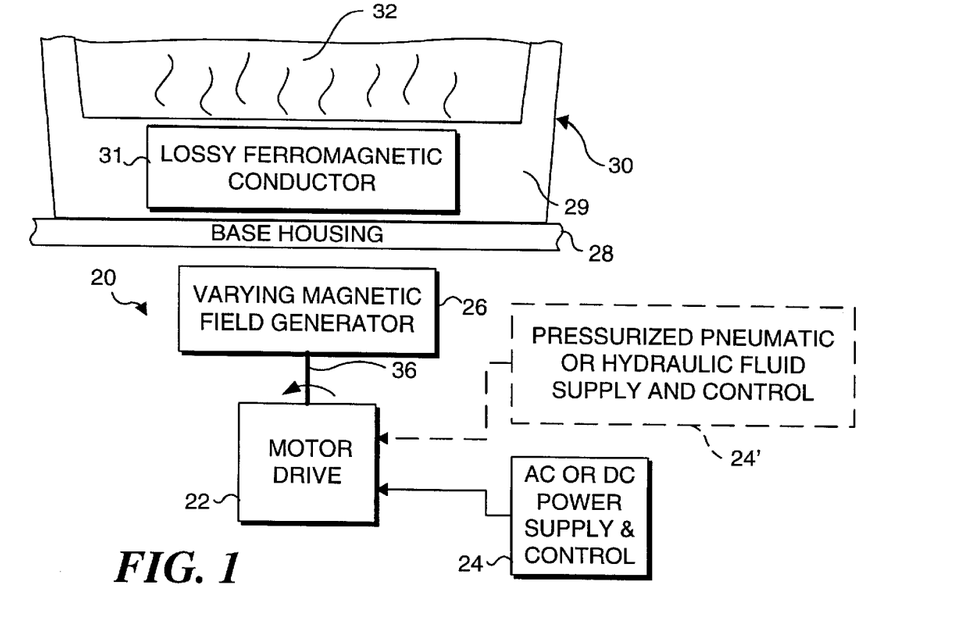
FIG. 1 is a block diagram functionally illustrating components of the present invention.

With reference to FIG. 1, a block diagram shown therein illustrates a typical application of the present invention. In this application, a flux generator base 20 includes a motor drive 22 that is energized from an alternating current (AC) or direct current (DC) power supply/control 24. Motor drive 22 comprises a prime mover that supplies a mechanical driving force to actuate a varying magnetic field generator 26. While the motor drive is preferably electrically energized, it is also contemplated that a pneumatic or hydraulic motor can alternatively be used as the prime mover. An alternative pressurized pneumatic or hydraulic fluid supply and control 24' is shown for use in controlling such a motor. By using a fluid drive motor, electrical current to and in the device is eliminated, which may be desirable in certain applications. However, an electrically powered motor is typically lower in cost and generally preferable. To provide electrical current to operate an electrical motor, power supply/control 24 is preferably energized by connection to an AC line source (not separately shown). However, a DC battery supply might be used in certain applications, for example, when power is provided by connection to an automotive electrical system.

The motor drive is coupled to the varying magnetic field generator through a drive shaft 36. The movement produced by the motor drive causes a variation in the magnetic field produced by magnetic field generator that continuously changes the magnetic flux through paths outside of flux generator base 20.

Flux generator base 20 is intended to produce a varying magnetic field that induces a corresponding electrical current to flow in a conductor made from a lossy ferromagnetic material. Suitable ferromagnetic materials include iron, cobalt, and nickel, and various alloys containing these elements. A ferromagnetic material exhibits magnetic properties when exposed to a magnetic field, thereby enabling the magnetic field to be coupled to the material. If the magnetic field is varying, an eddy current will be caused to circulate in the ferromagnetic material. The ferromagnetic conductor is disposed sufficiently close to the flux generator base to enable magnetic field coupling between the conductor and the flux generator to occur, thereby causing an eddy current to circulate in the ferromagnetic conductor. As the electrical eddy current circulates in the ferromagnetic conductor, part of the electrical energy is converted into heat, through current losses. If a "lossy" ferromagnetic material, such as a "soft" iron, is used for the ferromagnetic conductor, the current losses are primarily in the form of eddy current losses. The term "soft" iron as used herein and in the claims refers to an iron that maintains little or no magnetic properties after a magnetic field (that it was previously exposed to) is removed. In such materials, magnetic domains become aligned with the magnetic field when it is present, but these domains become relatively random when the external magnetic field is removed. The eddy current flowing through the conductor, and the associated eddy current losses increase as a function of the frequency of the varying magnetic field and the strength of the magnetic field. Since energy must be conserved, these eddy current losses generate heat that increases the temperature of the ferromagnetic conductor. Under suitable conditions, the ferromagnetic conductor temperature will increase up to a limit, known as the Curie temperature, at which point the ferromagnetic material loses its ability to be inductively coupled.

In one preferred application of the flux generator base, the varying magnetic field it produces passes through a housing 28 in which the varying magnetic field generator is disposed and into a base portion 29 of a container 30 in which a ferromagnetic conductor 31 comprising the lossy ferromagnetic material is disposed. The varying magnetic field is coupled into the ferromagnetic conductor, causing eddy currents. The losses due to the eddy current increase the temperature of the ferromagnetic conductor, which in turn, heats the container base, thereby transferring heat to a beverage 32 held within the container. Preferably, housings 28 and 29 comprise material through which magnetic flux readily passes, such as a plastic, fiberglass, or a composite material. A typical separation between varying magnetic field generator 26 and conductor 31 is on the order of from about 0.1 cm to about 2.0 cm.

Figure 2:
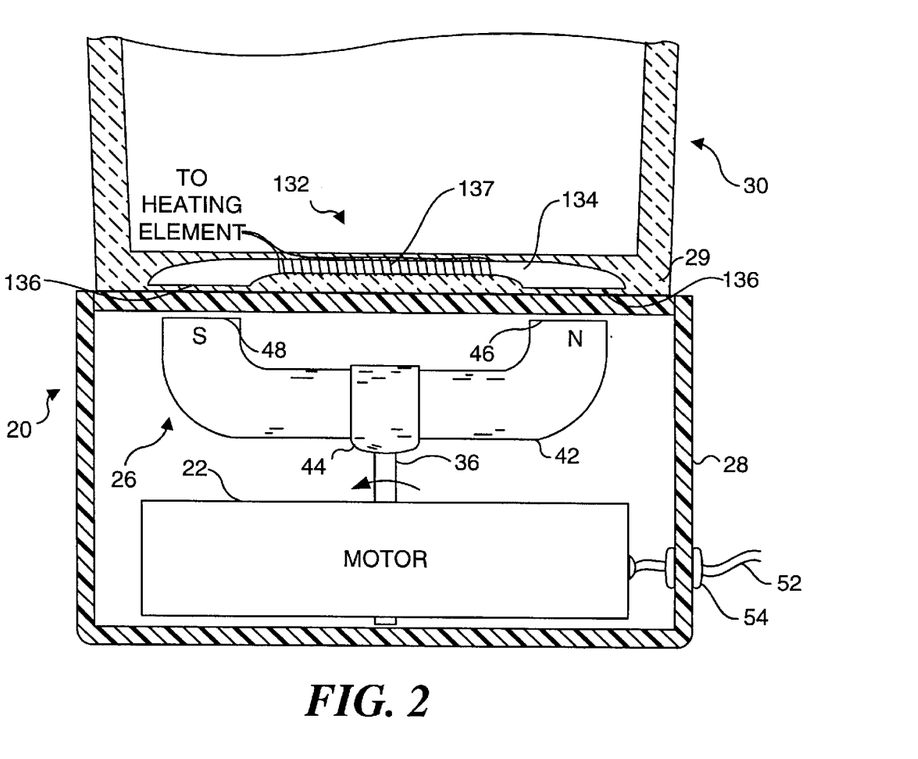
FIG. 2 is a cut-away side elevational view of a first embodiment of the present invention.

FIG. 2 illustrates a first embodiment of flux generator base 20 that includes a motor drive 22 disposed within a housing 28. Motor drive 22 is coupled to a generally elongated U-shaped permanent magnet 42 through rotating drive shaft 36. The rotating drive shaft connects to a collar 44 around the midsection of permanent magnet 42. Preferably in this and in each of the other embodiments of the present invention described below, the permanent magnet is formed of a neodymium-iron-boron alloy or other rare earth or metal alloy that produces a relatively high magnetic flux density. Other types of ferro-magnetic alloys are also acceptable for this purpose, although it is generally desirable to use a material for the permanent magnet(s) that produces a relatively strong magnetic field. Permanent magnet 42 includes a north pole face 46 and a south pole face 48 that face upwardly and are disposed immediately adjacent the interior side of the lower surface of housing 28 (as depicted in the Figure). To prevent undesired shunting of the magnetic flux between north pole face 46 and south pole face 48 and eddy current losses that would occur if a conductive material were used, housing 28 preferably comprises a plastic polymer material that is a good electrical insulator and does not block the magnetic flux produced by the permanent magnet. An electrical current appropriate to energize the motor drive is supplied through electrical leads 52, which pass through a grommet 54 disposed in the side of housing 28.

The magnetic flux produced by permanent magnet 42 is coupled into an overlying ferromagnetic conductor 132, comprising a core 134 and two faces 136 spaced apart so as to substantially match the spacing between the north and south poles of permanent magnet 42. As the permanent magnet is rotated by the motor, the north and south poles pass beneath faces 136, thereby generating an eddy current circulating through core 134. As the eddy current circulates through the ferromagnetic conductor, significant eddy-current losses result, thereby raising the temperature of ferromagnetic conductor, so that the heat it produces is transferred into a liquid or other material held within container 30.

In an optional configuration, core 134 may be wound with a wire coil 137, which is connected to a heating element that is disposed in the container (e.g., in the base of the container or in a sidewall of the container near its base) to heat the liquid in container 30. As current flows through core 134, a current is induced in wire coil 137, thereby providing energy to the heating element.

Figure 3A:
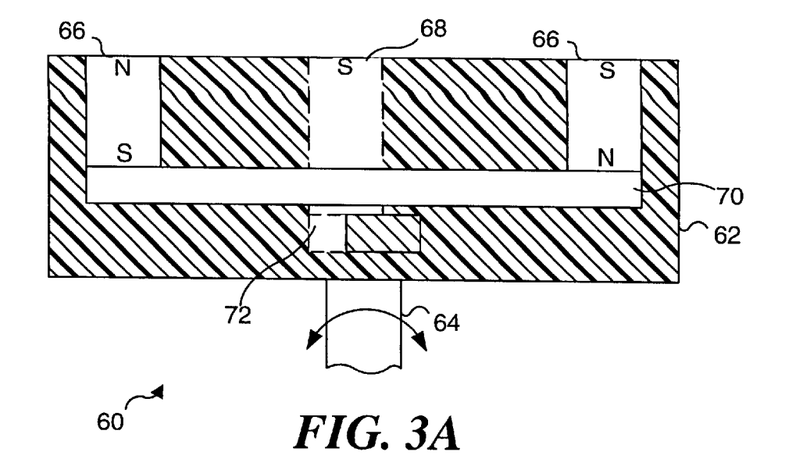
FIGS. 3A and 3B respectively illustrate a cross-sectional elevational view and a top plan view of a second embodiment of a variable magnetic flux generator that includes two sets of permanent magnets.
Figure 3B:
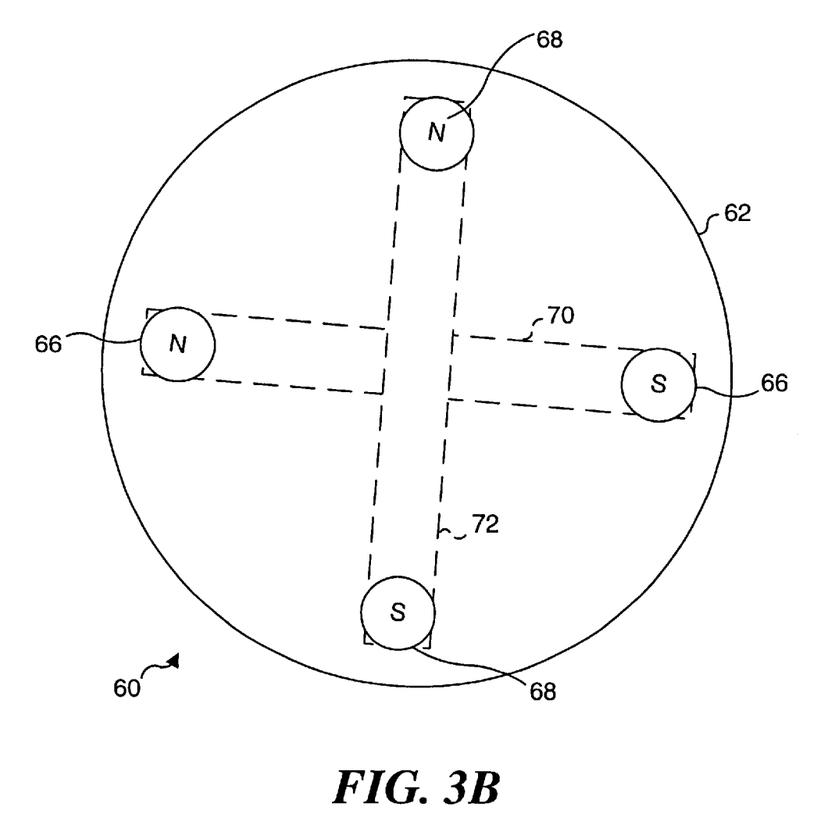

FIGS. 3A and 3B show an alternative embodiment of a varying magnetic field generator 60. In these Figures, the housing and motor drive of the base are not illustrated, but it will be apparent that a housing such as housing 28 can enclose varying magnetic field generator 60. A motor drive is coupled to a drive shaft 64 to rotate a disk 62, which comprises the varying magnetic field generator, in either direction about a longitudinal axis of drive shaft 64. Embedded within disk 62 are two sets of permanent magnets 66 and 68; the north pole face of one of these permanent magnets and the south pole face of the other permanent magnet are generally flush with the upper surface of disk 62 (as shown in the Figure). A flux linkage bar 70 extends between the south and north pole faces of permanent magnets 66 (within disk 62), while a flux linkage bar 72 extends between the north and the south pole faces of permanent magnets 68 (within disk 62). The relationship of the permanent magnets and flux linkage bars are best illustrated in FIG. 3B. It will also be apparent that additional permanent magnets can be included within disk 62 at spaced-apart intervals.

Rotation of disk 62 about its central axis in either direction varies the magnetic field experienced by ferromagnetic conductor 132 (shown in FIG. 2) and alternately changes the polarity of the field as the different permanent magnets rotate to positions adjacent to the pole faces of the ferromagnetic conductor. The varying magnetic field that is thus produced by rotation of disk 62 induces an eddy current to circulate in the ferromagnetic conductor, thereby producing eddy-current losses and generating heat. The speed at which disk 62 rotates changes the frequency and magnitude of the electrical eddy currents induced in the ferromagnetic conductor. It is contemplated that disk 62 can be rotated at a rate such that the frequency of the eddy currents induced to circulate in the ferromagnetic conductor is more than 10 kHz.

It should be noted that the energy transferred to the ferromagnetic conductor (and resultant heat generation) increases as the rotational speed of the varying magnetic field generator increases. Also, as the relative spacing between varying magnetic field generator 60 and the ferromagnetic conductor changes, the amplitude of the induced electrical current also changes, i.e., the magnitude of the induced electrical current increases as the separation decreases. While not shown in any of the Figures, it will be apparent that the separation between rotating disk 62 and the ferromagnetic conductor can be readily changed to selectively determine the maximum current induced in the ferromagnetic conductor—all other parameters such as rotational speed remaining constant. Conversely, the spacing can be held constant, while the rotational speed of rotating disk 62 is changed to control the energy transfer to the ferromagnetic conductor.

At relatively slow rotational speeds, the rotation of one or more very strong permanent magnets directly below a ferromagnetic conductor may apply sufficient torque to the ferromagnetic conductor to cause the ferromagnetic conductor to move back and forth slightly. However, any movement or vibration of the ferromagnetic conductor due to such torque will be substantially eliminated when the ferromagnetic conductor is attached to the beverage container. Furthermore, if the rotational speed of the varying magnetic field generator is sufficiently high, the effects of any torque applied to the ferromagnetic conductor will be almost imperceptible. It should also be noted that the magnetic field coupled to the ferromagnetic conductor provides a varying attractive force between the flux generator base and the ferromagnetic conductor, thereby helping to hold the beverage container in place on the flux generator base.

Figure 4A:
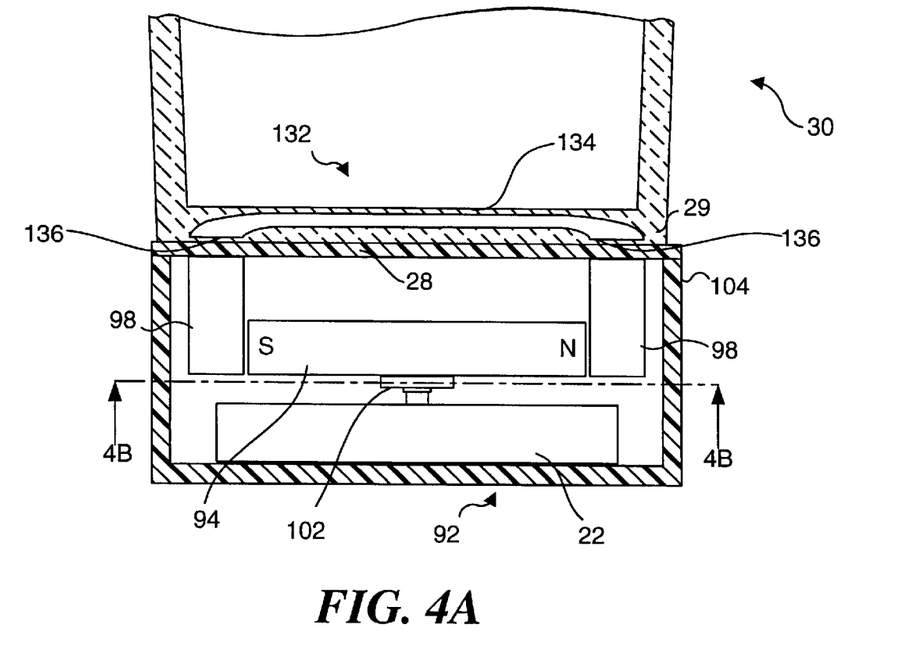
FIGS. 4A and 4B are respectively a side elevational cross-sectional view of another embodiment of a varying magnetic flux generator base magnetically coupled to a ferromagnetic conductor in a container, and a cross-sectional view of the varying magnetic flux generator base, taken along section lines 4B—4B in FIG. 4A.
Figure 4B:
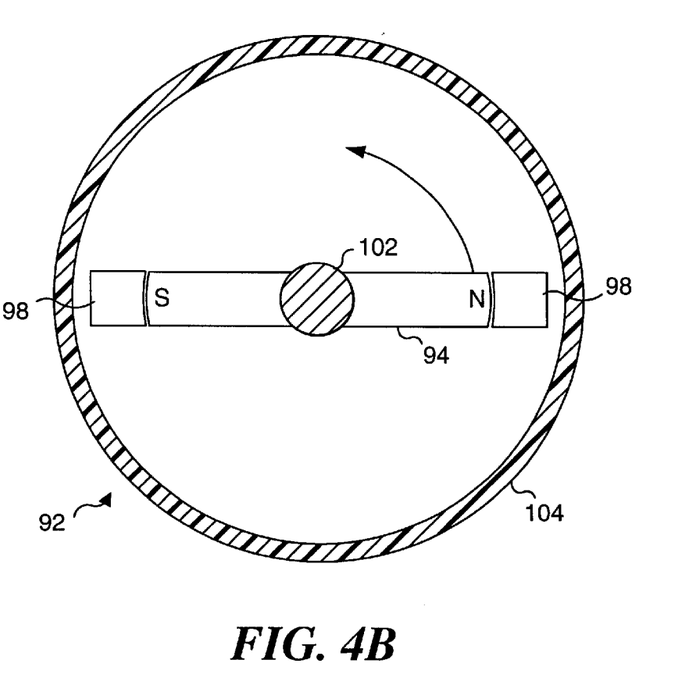

In FIGS. 4A and 4B, a flux generator base 92 is illustrated that eliminates virtually all rotational torque on the ferromagnetic conductor. In this embodiment, a permanent magnet 94 is coupled through a connection 102 to the shaft of a motor 22. The motor, permanent magnet, and connection are all disposed in a cylindrical-shaped housing 104 of flux generator base 92. Cylindrical-shaped housing 104 preferably is fabricated of a plastic polymer that does not block or shunt magnetic flux and which does not conduct eddy currents. Inside cylindrical-shaped housing 104, at diametrically opposite sides of the housing, are disposed two vertically aligned flux linkage blocks 98. As permanent magnet 94 rotates, its north and south poles pass adjacent to the bottom inwardly facing surfaces of flux linkage blocks 98, as shown clearly in FIG. 4B. The magnetic flux produced by permanent magnet 94 is conveyed through the flux linkage blocks and coupled into an overlying ferromagnetic conductor 132. Flux generator base 92 is disposed relative to ferromagnetic conductor 132 such that the upper ends of the flux linkage blocks are disposed opposite faces 136 of the ferromagnetic conductor. Since permanent magnet 94 rotates in a plane that is substantially spaced apart from the top of cylindrical-shaped housing 104 (as illustrated in the Figure), the rotating permanent magnet applies substantially less rotational torque on the overlying ferromagnetic conductor than would be the case if the permanent magnet were rotating in a plane closer to the receiver, e.g., immediately adjacent to the top of the cylindrical-shaped housing. Flux linkage blocks 98 tend to concentrate the magnetic flux produced by the rotating permanent magnet in a vertical direction, minimizing any horizontal component of the magnetic flux, so that little rotational force is experienced by adjacent faces 136 of ferromagnetic conductor 132.

Figure 5:
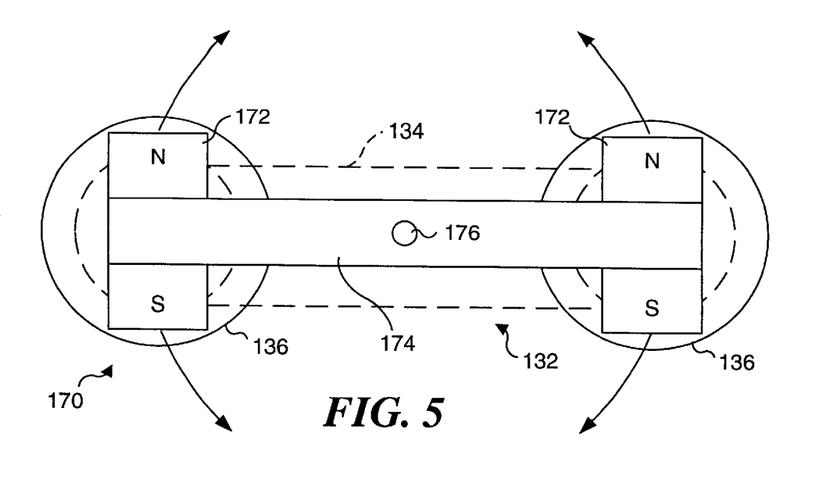
FIG. 5 is a bottom plan view of a varying magnetic flux generator (housing not shown), in which two permanent magnets are driven to reciprocate back and forth below the ferromagnetic conductor.

The embodiments of flux generator bases discussed thus far have all included permanent magnets that rotate. In FIG. 5, a flux generator base 170 is illustrated that includes a flux linkage bar 174 mounted to a shaft 176. Shaft 176 reciprocatively rotates back and forth, causing permanent magnets 172 to pass back and forth below faces 136 of ferromagnetic conductor 132. As the magnetic flux produced by the permanent magnets and experienced by ferromagnetic conductor 132 periodically changes due to the reciprocating movement of the permanent magnets back and forth below the faces of the ferromagnetic conductor, an electrical eddy current is induced to circulate within the ferromagnetic conductor.

Figure 6:
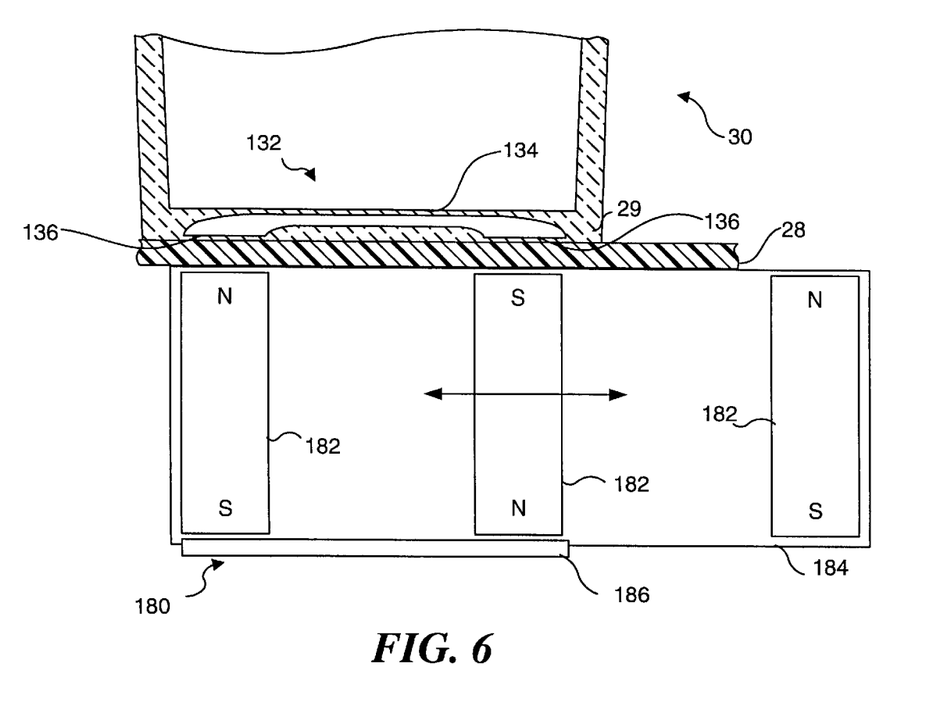
FIG. 6 is a side elevational view of a flux generator base (only a portion of the housing shown) in which three permanent magnets are driven to linearly reciprocate below the ferromagnetic conductor.

Instead of being rotatably reciprocated back and forth, the permanent magnets can be driven to reciprocate back and forth in a linear fashion, as in the embodiment of a flux generator base 180 illustrated in FIG. 6. In this embodiment, a flux shunt bar 186 is disposed below three vertically-aligned and spaced-apart permanent magnets 182 and extends over the respective north and south poles of two of the permanent magnets. The upward facing poles of permanent magnets 182 are respectively north, south, and north (or each can be of opposite polarity), in the order in which they are attached to a moving plate 184 that is reciprocatively driven back and forth. The spacing between permanent magnets 182 is such that at the two extreme linear positions of reciprocating plate 184, the poles of two of the permanent magnets are disposed immediately below faces 136 on ferromagnetic conductor 132; and, these poles are of opposite polarity. The linear reciprocating movement of moving plate 184 is provided by an appropriate drive mechanism (not shown), receiving its motive power from an electrical motor drive (also not shown), which is disposed either locally within the flux generator base, or remotely, coupled to the flux generator base by a drive shaft.

Figure 7:
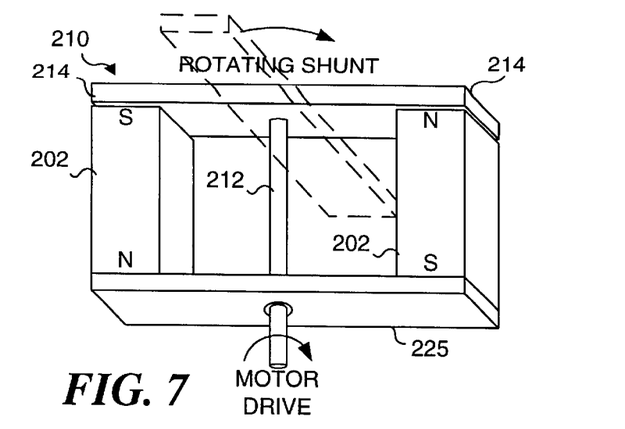
FIG. 7 is an isometric view of a varying magnetic flux generator (housing not shown), in which fixed permanent magnets and a rotating flux shunt bar are provided.

As shown in FIG. 7, a further embodiment of the varying magnetic field generator includes a fixed flux linkage bar 225 and a rotating flux linkage shunt 214 connected to a drive shaft 212 that rotates the flux linkage shunt in a plane above the pole faces of permanent magnets 202 (as shown in the Figure), so that it passes between the pole faces of the permanent magnets and the pole faces of the ferromagnetic conductor (not shown here). Fixed flux linkage bar 225 and rotating flux linkage shunt 214 are both fabricated of a metal or alloy with high magnetic permeability, which is thus characterized by its ability to substantially shunt magnetic flux. When rotating flux linkage shunt 214 is in the position represented by the phantom view (dash lines), i.e., in a position so that its longitudinal axis is oriented about 90° to the longitudinal axis of fixed flux linkage bar 225, the flux linkage between the permanent magnets and the ferromagnetic conductor is at a maximum, and when rotating flux linkage shunt 214 is in the position shown (by the solid lines) in FIG. 7, the magnetic flux produced by the permanent magnets is substantially shunted between them through the rotating flux linkage shunt and has little effect on the overlying magnetic flux conductor. Due to the resulting periodically varying magnetic flux coupled into the ferromagnetic conductor core, an electrical current is induced in the ferromagnetic conductor.

A desirable feature of the embodiment shown in FIG. 7 is that when the device is de-energized, leaving the magnetic flux shunted between the poles of the permanent magnets, very little magnetic field produced by the permanent magnets escapes outside the housing (not shown) around the flux generator base. The rotating flux linkage shunts thus serve to "turn off" much of the external magnetic field by shunting it between the poles of the permanent magnets.

Figure 8:
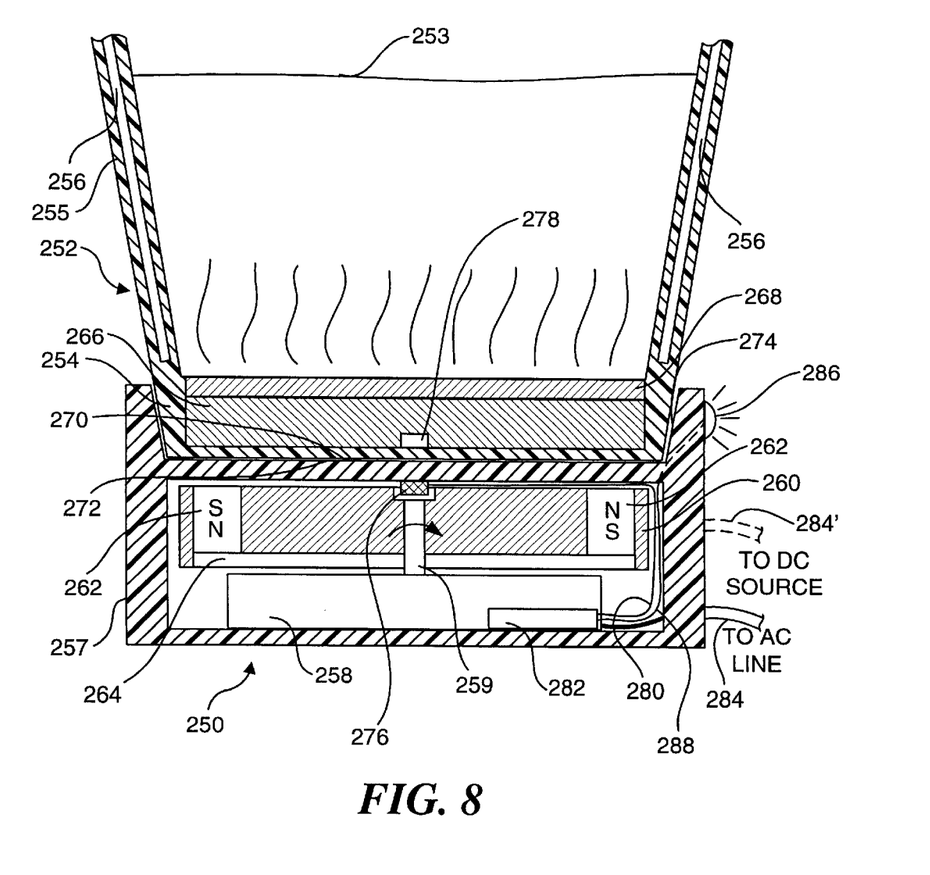
FIG. 8 is a cut-away side elevational view of another embodiment in which a container holding a liquid is heated through an magnetic energy transfer between a varying magnetic flux generator and a ferromagnetic conductor that is disposed in the base of the container.
Figure 9:
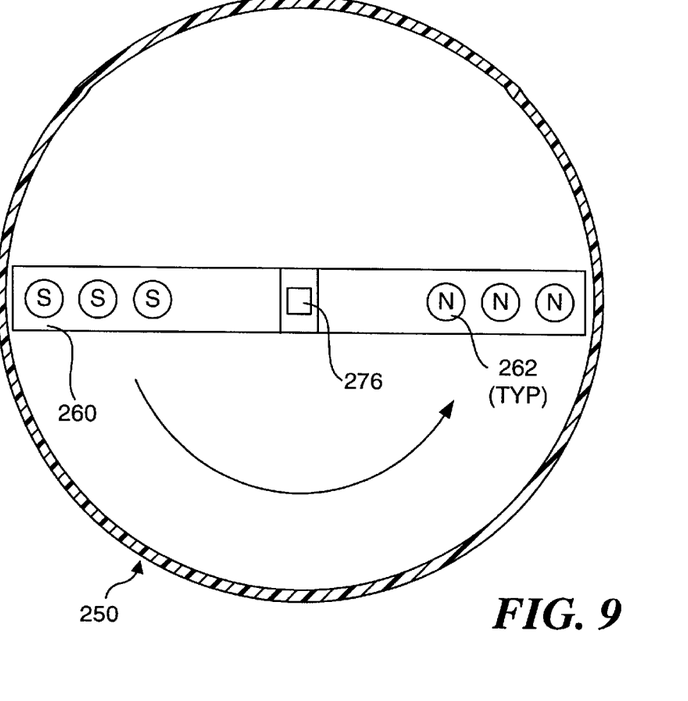
FIG. 9 is a top plan view of an embodiment of a rotor used in the variable magnetic flux generator shown in FIG. 8.

Another embodiment of the present invention suitable for warming a beverage or other material is shown in FIG. 8. This embodiment includes a flux generator base 250, and a cup 252 that is adapted to hold a beverage 253 (or other substance). The flux generator base comprises a housing 257, a pancake electric motor 258 that drivingly rotates a shaft 259, and a rotor 260 that is driven by the shaft. Preferably embedded in the rotor (or otherwise attached thereto) are a plurality of permanent magnets 262. The magnets on one side of the rotor are oriented with their north pole faces facing upwardly, while the magnets on the diametrically opposite side of the rotor have their south pole faces facing downwardly of the rotor. In an alternative configuration, a plurality of pairs of magnets are disposed at different radii from the shaft may be used, as shown in FIG. 9. In this instance, the plurality of magnets are arranged such that each pair comprises an upwardly facing north pole on one side and an upwardly facing south pole on the diametrically opposite side. The rotor may also include a flux linkage bar 264, that operates in a manner similar to that of the flux linkage bars described above. It is preferable that the components comprising the flux generator be of low profile, so that the external configuration of the base device is relatively short compared to its diameter.

The cup comprises a base portion 254 joined to an upper portion 255. The upper portion preferably defines a sealed interior cavity 256 that is preferably filled with an insulating material, or simply filled with air, forming a "dead air space." Preferably, the upper portion of the cup should be made of a material with a low thermal conductivity, such as various plastic materials that exhibit good thermal insulating properties.

As with the foregoing embodiments of the base unit, a varying magnetic field is generated when the permanent magnets are rotated by the motor. This magnetic field is inductively coupled into a disk-shaped ferromagnetic conductor 266, preferably made of a lossy ferromagnetic material such as soft iron, which is embedded in the base of cup 252. Preferably, a similarly-shaped disk 268 of stainless steel (or other corrosion-resistance metal with a high thermal conductivity) is also embedded in the cup base so that it is in thermal contact with both the ferromagnetic conductor disk and the beverage (or other substance in the cup) and is sealed around the edges to form a bottom of the interior of the cup that prevents the beverage from coming into contact with the ferromagnetic conductor disk. Optionally, the base portion of the cup may comprise a non-metallic material with a relatively high thermal conductivity. In this configuration, heat is readily transferred from the ferromagnetic conductor to the beverage (or other substance in the cup) via the stainless steel disk or non-metallic material, but the beverage does not come into contact with the ferromagnetic conductor, thereby eliminating potential rust and/or contamination problems.

In order to provide optimal energy transfer to the cup, the cup should be properly "mated" to the flux generator base unit. Preferably, the cup should have a flat bottom 270 that is placed on top of a flat interface surface 272 defined on the top of flux generator base 250. In addition, it is preferably that the top of the flux generator base define a generally cylindrical receptacle 274, which is adapted by its size and shape to receive the cup, as shown in the Figure.

For safety reasons, as well as to save power and operational wear, it is desirable for the flux generator base to operate only when there is a cup present within receptacle 274. When a cup is not present, the flux generator base preferably should be in a low-power-consuming "sleep" mode. Therefore, the flux generator base must be able to sense when a cup is present, so that it can "wake up" and begin warming the beverage, and able to sense when the cup has been removed, so that the flux generator base can turn off and go back to "sleep." The ability to detect the presence of the cup in receptacle 274 can be achieved in a variety of ways. For example, a Hall-effect sensor 276 (or a magnetic reed switch) is mounted in the flux generator base, and a magnet 278 is disposed in the center of the cup base so that the magnet is in close proximity to the Hall-effect sensor (or reed switch) when the receiver unit is placed on the flux generator base. The magnetic field produced by magnet 278 is sensed by the Hall-effect sensor (or reed switch), causing a change in the output signal of the sensor. (The change in the output signal of the sensor will depend on whether the sensor provides a normally-open or normally-closed switch condition in response to a magnetic field). This sensor output signal is conveyed through a lead 280 to a motor control 282 and enables the motor control to respond to the cup being present in the receptacle, so that it energizes the motor to heat the beverage in the cup, when the cup is present. Preferably, the Hall-effect sensor (or reed switch) should be positioned in the center of the rotating magnetic field so that it is not unduly affected by the rotating magnetic field. Similarly, magnet 278 should be disposed generally in the center of the cup base, to ensure it will be in close proximity to the Hall-effect sensor when the cup is disposed in receptacle 274 of the flux generator base.

Pancake motor 258 is supplied with an electrical current through either a lead 284, which is connected an AC power source, or alternatively (and assuming that the pancake motor is designed to instead be energized by 12 volts DC), through a lead 284', which is connected to a DC power source, such as an automobile cigarette lighter receptacle. Optionally, in cases where the flux generator base is provided as part of a vehicle, lead 284' may be connected to the vehicle's electrical system via a connector disposed in proximity to the flux generator base. If the pancake motor is energized by DC power, lead 284' will preferably be connected to a plug (not shown) that is adapted to mate with a conventional automobile cigarette lighter receptacle. Supplying current to the motor (either AC or DC, depending upon the embodiment in use) will cause rotor 260 to rotate, generating a varying magnetic field.

It is preferable that when the Hall-effect sensor signal (or reed switch) changes state to indicate that the cup has been positioned in receptacle 274 of the flux generator base, an indicator light 286 that is disposed on the flux generator base will be energized with current supplied through a lead 288 by motor control 282. When thus energized, this indicator light will alert a user that the base unit is in an operational mode, i.e., heating the beverage or other substance contained in the cup.

Figure 10:
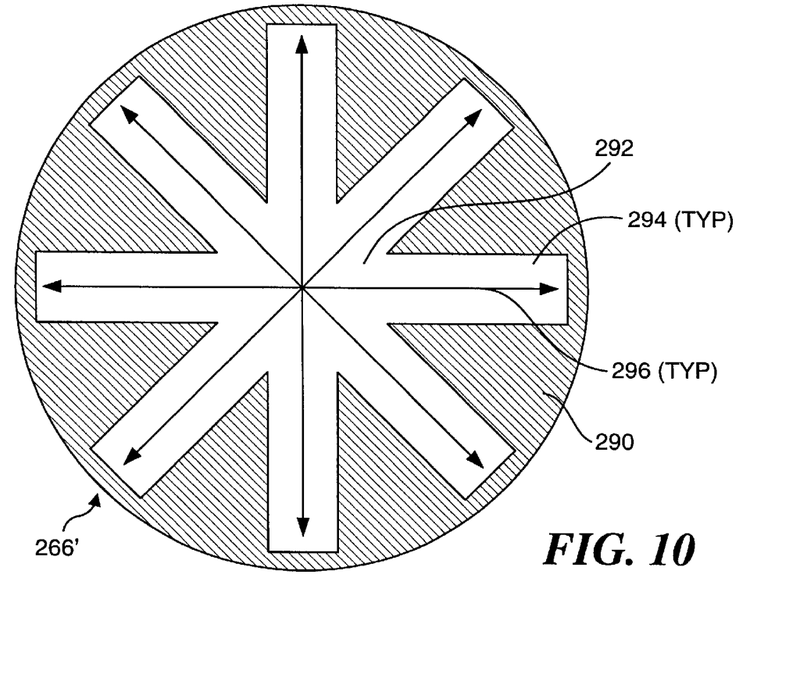
FIG. 10 is a top plan view of a ferromagnetic conductor, suitable for use in the embodiment of FIG. 8.

An alternative configuration of the ferromagnetic conductor is shown in FIG. 10. A ferromagnetic conductor 266' comprises a disk 290 in which a "star" shaped ferromagnetic conductor 292 comprising a plurality of radially extending arms 292 is embedded. Disk 290 preferably comprises a material that has a relatively high thermal conductivity but little (or no) ferromagnetic properties. Optionally, ferromagnetic conductor 292 may be embedded in the base portion of a cup or other container, so that 290 comprises the base of the cup. Since the disk material has a high thermal conductivity, it readily transfers heat from the ferromagnetic conductor to the base of the cup.

In the foregoing description, various embodiments of the invention are presented in which a beverage is heated. This disclosed application of the invention is by way of example, and is not meant to be limiting of its contemplated uses, as the invention is equally well-suited for other applications in which a conventional hot plate or thermally heated surface might be used to heat a substance, including heating or warming foods (e.g., soup or chili), heating chemicals, etc. It is also contemplated that the present invention can readily be incorporated into a cook top or on a surface portion of a range and used for heating various foods or other materials.

Although the present invention has been described in connection with the preferred forms of practicing it and modifications thereto, those of ordinary skill in the art will understand that many other modifications can be made to the invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for heating a substance, comprising:
   (a) a container adapted to hold the substance, said container including:
      (i) a base portion;
      (ii) a ferromagnetic conductor disposed within the base portion; and
      (ii) an upper portion connected to the base portion, said upper portion being adapted to receive the substance so that the substance is in thermal heat transfer relationship with the base portion of the container; and
   (b) a flux generator including:
      (i) a housing adapted to support the base portion of the container;
      (ii) a varying magnetic field generator that includes at least one permanent magnet and is disposed within the housing of the flux generator; and
      (iii) a prime mover drivingly coupled to an element of the magnetic field generator, causing said element of the magnetic field generator to move relative to the ferromagnetic conductor, movement of said element of the magnetic field generator producing a varying magnetic field that induces an electrical eddy current to circulate within the ferromagnetic conductor, thereby generating heat due to eddy current losses, so that the substance in the container is heated by the heat transferred through the base portion of the container.

2. The apparatus of claim 1, wherein the prime mover comprises an electric motor.

3. The apparatus of claim 1, wherein said at least one permanent magnet is mounted on the element that is moved by the prime mover, movement of said at least one permanent magnet generating the varying magnetic field experienced by the ferromagnetic conductor.

4. The apparatus of claim 1, wherein said at least one permanent magnet includes a rare earth alloy.

5. The apparatus of claim 1, wherein the varying magnetic field generator includes a plurality of permanent magnets and a movable support on which the plurality of permanent magnets are mounted, said prime mover causing the movable support to move relative to the ferromagnetic conductor, thereby varying the magnetic field along a path that includes the ferromagnetic conductor.

6. The apparatus of claim 5, wherein the movable support is caused to reciprocate back and forth in a reciprocating motion.

7. The apparatus of claim 1, wherein the element of the magnetic field generator that is drivingly coupled to the prime mover comprises a magnetic flux shunt that is moved by the prime mover, to periodically shunt a magnetic field produced by said at least one permanent magnet of the varying magnetic field generator, causing the magnetic field produced by said at least one permanent magnet to vary along a path that includes the ferromagnetic conductor.

8. The apparatus of claim 1, further comprising an adjustment member that is selectively actuated to control a speed with which the element of the magnetic field generator is moved.

9. The apparatus of claim 1, wherein the upper portion of the container includes a thermally insulating layer.

10. The apparatus of claim 9, wherein the thermally insulating layer of the upper portion of the container comprises an external wall and an internal wall separated by a sealed air space.

11. The apparatus of claim 1, wherein a receptacle is defined in the flux generator housing, said receptacle having a size and shape adapted to receive the base portion of the container.

12. The apparatus of claim 1, wherein the ferromagnetic conductor comprises a soft iron metal.

13. The apparatus of claim 1, further comprising:
(a) a coil of wire wrapped around the ferromagnetic conductor; and
(b) a heating element connected to the coil of wire and disposed in the container so as to be in heat transfer communication with the substance in the container, wherein as current flows through the ferromagnetic conductor a current is induced to flow in the coil of wire that is used to energize the heating element to further heat the substance in the container.

14. Apparatus for heating a liquid, comprising:
(a) a flux generating base comprising:
(i) an electric motor having a drive shaft;
(ii) a rotor, operatively coupled to the drive shaft of the electric motor to be rotated thereby and having attached thereto a plurality of permanent magnets, each permanent magnet having a north pole face and a south pole face oriented generally parallel to a rotational plane of the rotor; and
(iii) a housing in which the electric motor and the rotor are disposed, a surface of the housing defining a supporting interface; and
(b) a container in which the liquid is held, including:
(i) a container base that rests on the supporting interface of the housing;
(ii) a ferromagnetic conductor disposed in the container base, and
(iii) an upper portion sealingly connected to the container base, said upper portion being adapted to hold the liquid in thermal contact with the container base, said motor rotating said rotor to produce a varying magnetic field that causes eddy currents to circulate within the ferromagnetic conductor when the container is resting on the supporting interface, said eddy currents producing heat that is transferred into the liquid through the container base at that time.

15. The apparatus of claim 14, wherein the supporting interface of the flux generating base is sized and shaped to receive the container base.

16. The apparatus of claim 14, further comprising a sensor disposed in the flux generating base that produces a signal indicative of whether the container base is resting on the supporting interface of the flux generating base.

17. The apparatus of claim 16, further comprising a permanent magnet disposed in the container base, said sensor comprising one of a Hall-effect sensor and a reed switch that changes the signal in response to the permanent magnet in the container base being position in proximity of said sensor when the container is rested on the supporting interface.

18. The apparatus of claim 16, wherein the electric motor is energized in response to the signal produced by the sensor, so that the rotor is only drivingly rotated by the electric motor when the container base is resting on the supporting interface of the flux generating base.

19. The apparatus of claim 14, further comprising an indicator that indicates when the electric motor in the flux generating base is operating.

20. The apparatus of claim 14, wherein the plurality of permanent magnets are disposed at different radii from a center of the rotor.

21. The apparatus of claim 14, wherein the electric motor is powered by a DC voltage supplied by a storage battery.

22. The apparatus of claim 21, further comprising an electric cord that includes an automobile cigarette lighter receptacle adapter at a first end and a second end connected to the electric motor, said electric cord supplying the DC voltage to the electric motor when the automobile cigarette lighter receptacle adapter is connected into an automobile cigarette lighter receptacle.

23. The apparatus of claim 14, wherein the container base further comprises a material having a high thermal conductivity that is disposed between the ferromagnetic conductor and the liquid and sealed around a periphery to the upper portion of the container so as to ensure that the liquid does not contact the ferromagnetic conductor, said material providing a thermal communication between the ferromagnetic conductor and the liquid.

24. The apparatus of claim 23, wherein said material comprises a disk fabricated of a corrosion-resistant metal.

25. The apparatus of claim 14, wherein the ferromagnetic conductor comprises a central portion connected to a plurality of arms that extend radially from the central portion.

26. The apparatus of claim 25, wherein the ferromagnetic conductor is embedded in a material comprising the container base that has a high thermal conductivity.

27. The apparatus of claim 14, wherein the ferromagnetic conductor comprises a soft iron metal.

28. The apparatus of claim 14, wherein the varying magnetic field develops an attractive force drawing the ferromagnetic conductor toward the supporting interface of the flux generating base so as to assist in maintaining the container base in contact with the supporting interface.

29. The apparatus of claim 14, further comprising:
(a) a coil of wire wrapped around the ferromagnetic conductor; and
(b) a heating element connected to the coil of wire and disposed in the container so as to be in heat transfer communication with the liquid, wherein as current flows through the ferromagnetic conductor a current is induced to flow in the coil of wire that is used to energize the heating element to further heat the liquid.

30. A method for heating a substance by inductively coupling a varying magnetic field to a ferromagnetic conductor disposed in a container that contains the substance, comprising the steps of:
(a) positioning a ferromagnetic conductor sealed within the container proximate to a supporting interface of a base;
(b) providing a magnetic field; and
(c) moving an element in the base with a prime mover so that the element is moved relative to the ferromagnetic conductor, a varying magnetic field that is produced thereby being inductively coupled to the ferromagnetic conductor, causing an electrical eddy current to circulate in the ferromagnetic conductor, thereby producing eddy current losses that generate heat in the ferromagnetic conductor, a portion of said heat being transferred to the substance to heat it.

31. The method of claim 30, wherein the step of providing the magnetic field comprises the step of providing at least one permanent magnet.

32. The method of claim 31, wherein the step of moving the element comprises the step of moving said at least one permanent magnet.

33. The method of claim 32, wherein the step of moving the element comprises the step of moving said at least one permanent magnet about an axis in a circular path to vary the magnetic field produced by said at least one permanent magnet along a path that includes the ferromagnetic conductor.

34. The method of claim 32, wherein the step of moving the element comprises the step of reciprocating said at least one permanent magnet back and forth to vary the magnetic field produced thereby along a path that includes the ferromagnetic conductor.

35. The method of claim 30, further comprising the step of enhancing a magnetic flux linkage between magnetic poles of the permanent magnet and the ferromagnetic conductor.

36. The method of claim 35, wherein the step of enhancing the magnetic flux linkage comprises the step of providing a flux linkage bar for coupling a magnetic field from a pole of said at least one permanent magnet into the ferromagnetic conductor.

37. The method of claim 30, further comprising the step of selectively varying a maximum magnetic field intensity that is coupled to the ferromagnetic conductor.

38. The method of claim 37, wherein the step of selectively varying the maximum magnetic field intensity comprises the step of changing a speed with which the element is moved.

39. The method of claim 30, wherein the step of providing the magnetic field comprises the step of providing a plurality of permanent magnets.

40. The method of claim 39, wherein the plurality of permanent magnets are fixed relative to the base, and wherein the step of moving the element comprises the step of intermittently passing a flux shunt member adjacent to pole faces of the plurality of permanent magnets so as to provide a magnetic flux shunt path between the pole faces of the plurality of permanent magnets, said magnetic flux shunt path periodically shunting the magnetic field to vary it.

41. The method of claim 39, wherein the step of moving the element comprises the step of moving the plurality of permanent magnets back and forth past the ferromagnetic conductor to vary the magnetic field experienced by the ferromagnetic conductor.

42. The method of claim 30, further comprising the step of providing an indication of whether the container is resting on the base.

43. The method of claim 30, further comprising the step of providing an indication of whether the prime mover has been energized.

44. The method of claim 30, wherein a coil of wire connected to a heating element disposed in the container is wrapped around the ferromagnetic conductor so that a current is induced in the coil of wire when current flows through the ferromagnetic conductor, said current that is induced in the coil of wire energizing the heating element.

* * * * *